United States Patent [19]

Detwiler et al.

[11] Patent Number: 4,936,303
[45] Date of Patent: Jun. 26, 1990

[54] ULTRASONIC HEATING APPARATUS AND METHOD

[75] Inventors: Sheldon P. Detwiler, Bellevue; George W. Keilman, Woodinville; Robert F. McConaghy, Kirkland, all of Wash.

[73] Assignee: UltraThermics, Redmond, Wash.

[21] Appl. No.: 123,218

[22] Filed: Nov. 20, 1987

[51] Int. Cl.$^5$ ............................................... A61F 7/00
[52] U.S. Cl. ................................. 128/399; 128/24 A
[58] Field of Search ...................... 128/24 A, 328, 660, 128/399; 73/642, 644

[56] References Cited

U.S. PATENT DOCUMENTS

| 3,387,604 | 6/1968 | Erikson | 128/24 A |
| 4,131,022 | 12/1978 | Mezrich | 128/660 X |
| 4,213,344 | 7/1980 | Rose | 73/642 X |
| 4,486,076 | 12/1984 | Taenzer | 128/660 X |
| 4,549,533 | 10/1985 | Cain et al. | 128/24 A |
| 4,586,512 | 5/1986 | Do-huu et al. | 128/660 |
| 4,622,972 | 11/1986 | Giebeler, Jr. | 128/24 A X |
| 4,646,756 | 3/1987 | Watmough et al. | 128/24 A X |

OTHER PUBLICATIONS

A Large Aperture Ultrasonic Array System for Hyperthermia Treatment of Deep-Seated Tumors, Seppi, et al., 1985 IEEE, 1985 Ultrasonics Symposium, pp. 942–948.
A Therapeutic Ultrasound System Incorporating Real-Time Ultrasonic Scanning, F. L. Lizzi, et al.; Copyright 1986 IEEE, 1986 Ultrasonics Symposium, pp. 981–984.

Primary Examiner—Francis Jaworski
Attorney, Agent, or Firm—Seed and Berry

[57] ABSTRACT

A method and apparatus for the treatment of tumors by heating with ultrasonic energy. A transducer assembly is provided in a housing having a refractive assembly disposed between the tumor and the transducer. The refractive assembly moves with respect to the transducer assembly. The refractive assembly includes one or more refractive elements. The refractive assembly is interchangeable to provide treatment of different types of tumors using the same transducer assembly and housing. The refractive assembly may focus, deflect or diffuse the ultrasonic energy depending on the arrangement of elements. Motion of the refractive assembly relative to the tumor results in a time-averaging spatial deposition pattern which is more highly uniform due to the averaging of maxima and minima which occurs in the near field.

26 Claims, 4 Drawing Sheets

ULTRASONIC HEATING APPARATUS AND METHOD

TECHNICAL FIELD

This invention relates to the field of therapeutic devices, and more particularly, to an apparatus and method for applying ultrasonic energy in a controlled pattern to cause heating within the body.

BACKGROUND ART

Laboratory tests have shown that certain tumors and cancerous tissue can be effectively treated by heat in excess of body temperature. Ultrasonic energy is presently used to create localized heating within the body for the treatment of many types of tumors. The temperature to which the tumors must be heated to effectively treat the cells is in the range of 43° –48° C. (109° –118° F.), but may vary somewhat, according to various factors.

A consideration in the use of ultrasonic devices to create localized heating is that the linear absorption coefficient of ultrasonic energy of bone is very large compared to that of a tumor being treated or surrounding muscle tissue. There is a 26% power absorption per millimeter of ultrasonic energy in bone at 1 MHz, increasing proportionately with the square of the frequency up to 2 MHz. There is only to 2.3% power absorption per millimeter of ultrasonic energy in muscle, with less frequency dependency. This can result in the bone becoming hotter than the tumor with moderate to severe bone pain. This may occur even if the bone receives less energy than the tumor or if the bone underlies the tissue which is being treated.

An ultrasonic hyperthermia treatment device is described in the 1985 Ultrasonics Symposium proceedings, pp. 942-948, IEEE, entitled "A Large Aperture Ultrasonic Array System for Hyperthermia Treatment of Deep-Seated Tumors," by Seppi et al. It has an array of transducers, each having a conical lens, mounted in a water bath. Each transducer is independently controllable in power, phase, and mechanical orientation. This device is bulky, complex, expensive, and difficult to operate.

A hyperthermia system using a transducer coupled with an ultrasonic imaging system is disclosed in an article titled "A Therapeutic Ultrasound System Incorporating Real-Time Ultrasonic Scanning," by Lizzi et al., the 1986 Ultrasonics Symposium Proceedings, IEEE, 981-984.

These devices and methods of operating them have numerous disadvantages. A transducer with or without a lens often creates an energy distribution pattern having multiple local minima and maxima in the near field. The depth, spatial location and strength of the minima and maxima vary with transducers, frequencies and lenses.

The near field linear intensity profile of a sample heating transducer with no lens is illustrated in FIGS. 1a–1d. These are lateral profiles measured 2 cm from the face of a 6 cm diameter unfocused transducer at different frequencies. The intensity profile at each frequency has minima and maxima that are non-uniformly distributed along the face of the transducer.

Figure 1A:
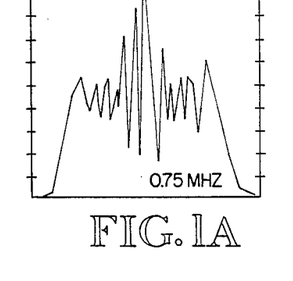
FIGS. 1a–1d are sample graphs of transducer linear intensity profiles.
Figure 1B:
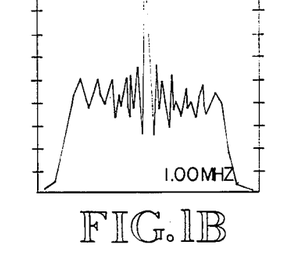
Figure 1C:
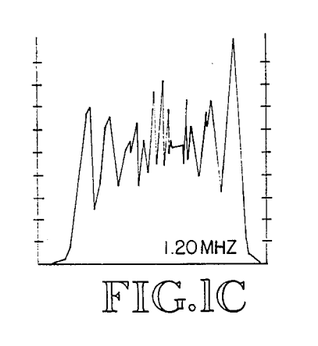
Figure 1D:
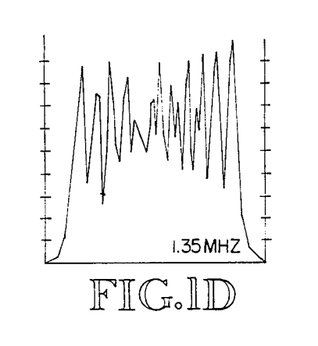

At 0.75 MHz the transducer energy profile has a minimum value at the center with two peaks on either side of the center as shown in FIG. 1a. At 1.00 MHz this transducer has an energy profile with a peak value in the center with various maxima and minima along the diameter as shown in FIG. 1b. At 1.20 MHz a peak value is at the far right hand side with a second peak in the center and a third, slightly lower peak at the far left hand side, as shown in FIG. 1c. At 1.35 MHz a more even distribution of maxima and minima is produced by the transducer but major variations in the intensity profile exist. These maxima and minima result in hot and cold spots in a region being treated with ultrasonic energy. Even small changes in frequency can significantly alter the intensity profile. Similarly, different transducers have different intensity profiles.

When high intensity energy, such as the peak in FIG. 1b, is repeatedly applied to tissue, the tissue heats excessively while other tissues received much less energy and are not heated. Similarly, an energy peak near the edge, such as in FIG. 1c, may inadvertently fall on healthy tissue or bone and cause undesirable heating and pain while the tumor is not sufficiently heated.

In some systems an array of transducers are used. Interactions between the sound fields of each transducer creates a complex linear intensity profile with additional maxima and minima created by the interaction. This results in greater variations in hot and cold spots and the location of each is more difficult to predict.

To aid in the elimination of undesirable interaction of sound fields from an array of transducers, the energy may be modulated in magnitude, phase or frequency. A second approach to prevent heating of localized regions of bone or tissue is to continuously move the transducer assembly in both a linear and pivoting manner (i.e. wobbling) so that the maxima and minima do not rest on any localized region for a significant period of time. Operator skill is critical in the manual manipulation of the transducer assembly. A less skilled operator may over heat bone without adequately treating the tumor.

DISCLOSURE OF THE INVENTION

It is an object of the present invention to provide an ultrasonic hyperthermia system for heating specific locations within the body with a controlled pattern of ultrasonic energy.

It is another object of the invention to provide a compact transducer and refractive assembly which can access a variety of different anatomical locations.

It is another object of this invention to provide an ultrasonic hyperthermia device whose correct operation is less dependent on operator skill than previous devices.

It is another object of the invention to provide a transducer with an interchangeable refractive assembly so that the same apparatus may by used to treat numerous different types of tumors.

Further, it is another object of this invention to provide a less costly apparatus for permitting treatment with a wide variety of ultrasonic heating patterns.

It is a further object of the invention to provide a refractive assembly which is non-symmetrical in a plane parallel to the direction of application of the ultrasonic energy.

These and other objects of the invention are accomplished by providing a transducer and refractive assembly within a single housing surrounded by the appropriate coupling fluid and enclosed by an acoustic membrane. The refractive assembly is placed in the ultrasonic field between the transducer and the tumor to be treated. The refractive assembly is moved relative to the transducer to scan or alter the ultrasonic energy pattern. Moving the refractive assembly relative to the transducer allows the time-averaged spatial deposition pattern to be highly uniform by averaging the maxima and minima that occur in the near fields of the transducer. An amplitude histogram having a desired mean value over contours of various complexities is produceable.

A different refractive assembly is usable for different types of tumors. For some types of tumors, a wedge-shaped element which provides a large area, even energy distribution pattern is most useful. For other types of tumors, a unitary refractive assembly having an array of refractive elements, each having different characteristics is useful. A refractive assembly which deposits energy on the surface of a sphere with little energy deposited in the center of the sphere is useful for some tumors. The refractive assembly may be a single element or an array of elements each having a different refractive pattern. The refractive assembly may be rotated, translated, oscillated or moved in a non-symmetrical or non-repeating pattern Alternatively, two refractive assemblies are provided. These may be coupled together and moved as a unit. Alternatively, the two assemblies are spaced apart and a drive motor is provided to move each of the assemblies independent of each other.

A unitary refractive assembly that includes a plurality of refractive elements arranged in a spiral creates an acoustic energy pattern useful in providing therapeutic treatment. The individual refractive elements focus energy on the surface of the tumor with less energy deposited in the center. The refractive assembly is rotated about an axis that is aligned with the main portion of the tumor. The maxima and minima from the transducer are refracted by each refractive element to impinge upon different tissues as the refractive assembly is rotated. This deposits average energy at the desired regions of the tumor. This permits treating of spherical or circular tumors using simple rotation of the refractive element rather than requiring a complex motion in two or more planes. Proper treatment is less dependent on operator skill and operator manipulation.

The transducer and refractive assembly may be directly coupled together and move as a unit or arranged to permit one to move independent of the other. An ultrasonic imaging probe in the same housing as the heating transducer assembly may also be provided.

BEST MODE FOR CARRYING OUT THE INVENTION

Treatment of tumors between the skin surface and several cm's in depth is accomplished using ultrasonic treating. The near field intensity profiles of these transducers contains excessive variations in maxima and minima as shown in FIGS. 1a–1d. The near field intensity profile extends from the tranducer face to approximately distance equal to the aperture diameter squared divided by four times the wavelength. For a 6 cm diameter transducer at 1 MHz this is 60 cm's. According to this invention treatment using near field energy is made possible by time-averaging the energy applied to the tumor. The acoustic intensity patterns from transducers such as those illustrated in FIGS. 1a–1d are modified by placing a refractive assembly in the pattern between the transducer and the region to be treated and moving the refractive assembly relative to the transducer.

Figure 3:
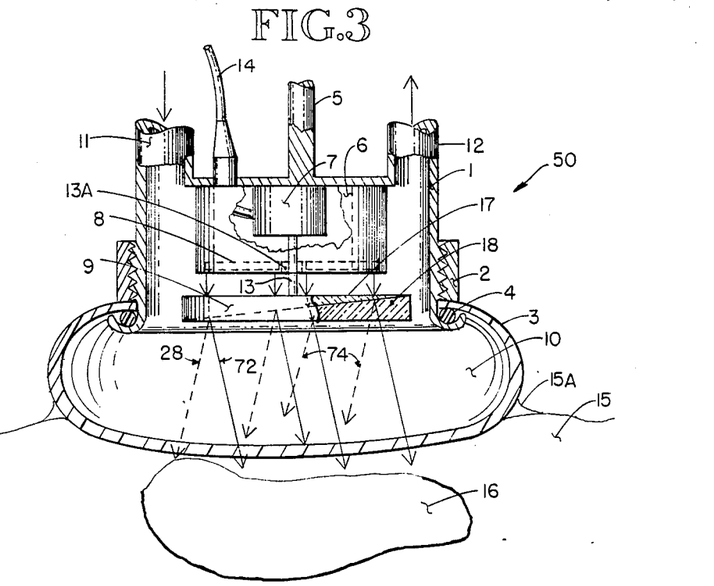
FIG. 3 is an elevated, partial, cross sectional view of an embodiment of the invention using a motor driven refractive assembly.

FIG. 2 illustrates various types of transducer refractive assemblies. FIG. 2a illustrates a transducer 19a with no refractive assembly being used. The intensity profile produced by this transducer in the near field is similar to those shown in FIGS. 1a–1d. FIG. 2b is a spherical, conical, acoustic refractive assembly comprising a single lens which focuses the energy from transducer 19a to a specific point. For a spherical, refractive assembly of the type shown in FIG. 2b the assembly may not overcome the variations in near field maxima and minima. It could be moved in a pattern to time-average the energy deposition over the tumor. Refractive assemblies such as that shown in FIG. 2b may also be made of different materials with tapers therebetween as shown in FIG. 3, to provide for deflection, or partial focus with some deflection rather than focus to a point of the ultrasonic energy A multifaceted acoustic refractive assembly 20 is shown in FIGS. 2c and 2e, FIG. 2e being the front view of FIG. 2c. The faceted refractive assembly 20 having various acoustical facets or elements 22, focuses the ultrasonic energy to a spheroidal volume, rather than to a point with less energy directed to the center of the sphere.

Figure 2A:
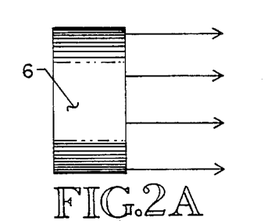
FIGS. 2a–2f are side and frontal views of a transducer and various refractive elements.
Figure 2B:
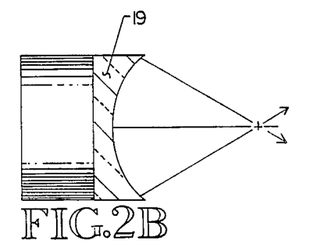
Figure 2C:
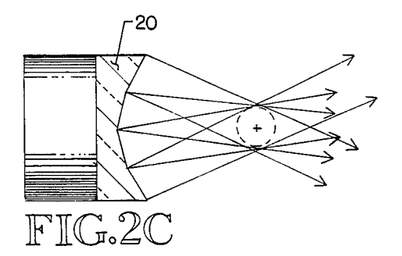
Figure 2D:
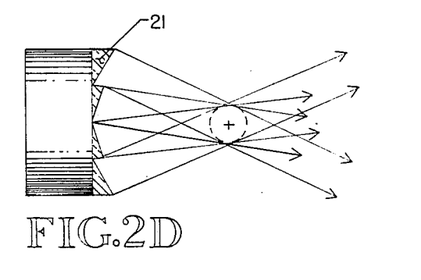
Figure 2E:
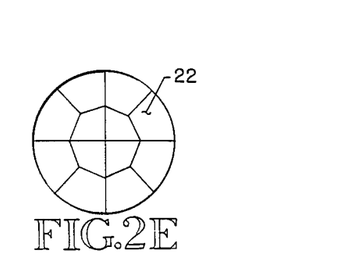

FIG. 2d illustrates a Fresnel type acoustic refractive assembly which provides a focusing similar to assembly 20, but with lower energy losses in the outer part of the lens.

Figure 2F:
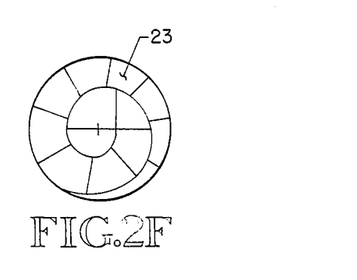

A spiral refractive assembly is illustrated in FIG. 2f. The refractive assembly 23a of FIG. 2f has numerous facets or elements 23 arranged in a spiral pattern. A spiral pattern of elements is one that provides small changes in energy deposition patterns from one element to another, yet avoids having multiple elements with deposition symmetry with respect to a central rotational axis. As a result, the refractive assembly more evenly averages the energy deposition over a tumor.

The facets 23 are formed in a spiral pattern according to a Fresnel lens design or other type of faceted acoustical lens. The spiral relationship is made using a plano-plano, plano-concave or plano-convex array of facets of different sizes and acoustical properties. The direction of movement may be vertical, lateral, rotational, pivotal, or combinations thereof.

The facets in the refractive assembly are arranged to cause time-averaged deposition to be spatially uniform for the particular relative motion. Each element in the refractive assembly has a different refraction pattern than any other element in the refractive assembly. Alternatively the elements may have similar or identical refraction patterns, each element being placed at a different location in the integral retractive assembly relative to the type of motion for that assembly. This provides nonsymmetry of an integral refractive assembly. Symmetry is avoided in the direction of motion in order to achieve the greatest amount of spatial averaging. This permits simple motion to provide the time averaged energy deposition. If the refractive assembly is rotated, effective time-averaged energy deposition is achieved by minimizing or eliminating radial symmetry. Similarly, for linear motion, linear symmetry is minimized and for axial motion (pivoting), axial symmetry is minimized. Some symmetry is permissible but not optimal. The treatment is most effective when the amplitude histogram of a given area has a desired mean value. For uniform heating the desired mean value is the same at all locations within the tumor boundary.

The refractive assembly of FIG. 2f lacks radial symmetry permitting rotational motion to average the energy deposition. The refractive assembly 20 of FIG. 2e has radial symmetry. The acoustical pattern generated by assembly 20 under simple rotational motion will have maxima and minima from the transducer which strike corresponding portions in the body. If this assembly having radial symmetry is rotated about a central axis the maxima and minima from the transducer through each element will impinge upon the same tissue throughout the rotation and will not average the maxima and minima thus permitting hot and cold spots in the underlying tissue. This same problem may occur with an array of transducers each having a lens, the transducers being in a symmetrical arrangement. By placing the elements on the refractive assembly in a pattern such that the maxima and minima of the transducer through a facet do not fall on corresponding tissue as the maxima and minima of another facet when the assembly is moved more uniform heating is possible. This permits energy to be uniformly deposited on the tumor about a central axis during rotation. In the alternative, a symmetrical retractive assembly is mounted off center to rotate eccentrically or in a combination of linear, rotational or pivoting motions.

FIG. 3 shows a ultrasonic treatment assembly labeled generally as 50, including a body under treatment 15 and a tumor mass 16 to be treated. The tumor 16 is of the type which is large in surface area and relatively thin. An example of this type of tumor is found in recurrent breast cancer.

The ultrasonic assembly 50 includes a housing 1 and a coupling membrane 3. The membrane 3 is connected to the housing 1 by use of a threaded ring 2 and a sealing element 4. Threaded ring 2 holds membrane 3 in a sealed relationship around the housing 1. Rotating the ring tightens or loosens it to remove or replace membrane 3. The entire hyperthermic assembly is connected to a moveable mount arm through support 5. The entire assembly is small enough to be suspended from a mount arm having joints and positionable with respect to various parts of the body. The transducer assembly includes an internal case 6 having a drive motor 7 and transducer assembly 8 mounted therein. The transducer may be a single transducer or transducer assembly comprised of two or more transducer elements. The refractive assembly 9 is removably connected to the drive motor 7 through shaft 13 having a seal 13a to prevent the circulating fluid from entering the case 6. The membrane 3 provides acoustical coupling of the ultrasonic energy from the assembly to the human body. An appropriate coupling gel 15a is used therebetween as required Surrounding the case 6 is an ultrasonic coupling fluid 10 which circulates within the assembly 50. The ultrasonic coupling fluid 10 has a low acoustic attenuation and the proper acoustical impedance for matching with the transducer, refractive element, and the coupling membrane 3. The fluid 10 enters through an inlet 11 and exists through an outlet 12. The fluid is circulated and temperature controlled to provide a constant surface temperature of the body at the temperature desired for treatment. The fluid also removes heat generated by the transducer element 8 and provides uniform temperature throughout the assembly 50. Air bubbles are removed from the fluid while it is circulated to ensure that no air bubbles build up on transducer 8 or occur with the housing. The volume and pressure of fluid 10 is adjustable. The membrane 3 is compliant, permitting the contour of the membrane 3 to vary for different anatomical sites.

The refractive assembly 9 is a disk having a tapered interface between two complementary refractive elements made of different types of refractive material. The refractive assembly includes an upper wedge-shaped disk element 17 and lower wedge-shaped disk element 18. The upper wedge-shaped disk 17 is a high-velocity acoustical material and has a longitudinal velocity higher than the fluid 10, a low acoustic attenuation, and an acoustical impedance similar to that of fluid 10, to provide good matching characteristics. This material may be a EL-34A syntactic foam available from Grace Syntactics, Inc. of Canton, Mass. The tapered disk 18 is a low velocity disk having a longitudinal velocity of sound substantially lower than fluid 10 with a low acoustic attenuation and a proper acoustic impedance match to fluid 10 and tapered disk 17. The tapered disk 18 may be made from Sylgard 170 silicone compound available from Dow Corning Inc. of Midland, Mich. The two complementary tapered refractive elements 17 and 18 are placed together to form a unitary refractive assembly 9. The entire refractive assembly is mounted on rotating shaft 13 to the transducer assembly. In addition to circular motion about a point some linear or pivoting motion may be provided to refractive assembly 9 to provide desired application of ultrasonic energy.

The refractive assembly 9 deflects the ultrasonic energy from transducers 8 by an angle theta. Rotation of the refractive assembly 9 causes a conical deflection of the ultrasonic field having an angle difference of two times theta, as illustrated by ultrasonic wave directional lines 72 and 74.

The rotating refractive assembly 9 is used to time-average the energy deposited from the ultrasonic transducer. Such an unfocused device is useful to provide uniform heating of large-area lesions. Without use of a refractive assembly the acoustic maxima and minima which occur in the near field of hyperthermia transducer often results in hot and cold regions. This adversely affects efficiency and causes pain in some regions, particularly in bones. The use of the rotating wedge assembly displaces the acoustic diffraction pattern, resulting in a more uniform time-averaged deposition of energy. This provides more uniform treatment for the tumor cells and minimized damage to healthy cells for large area lesions.

This particular wedge-shaped refractive assembly 9 has only one radial plane of symmetry. The timeaveraging deposition provided by this element is sufficient to permit simple rotational motion. This assembly does not have cross sectional or linear symmetry. Alternatively, a variety of different refractive assemblies or elements may be interchanged with this refractive assembly on shaft 13. These may focus, deflect or diffuse the acoustic energy. Refractive elements of the type described in FIGS. 2a–2f and FIG. 6 are usable herewith.

The shaft 13 on which refractive elements 17 and 18 are mounted may alternatively, have an inner shaft that is stationary or rotates relative to an outer shaft. In this embodiment one of the refractive elements, 17, is mounted on the outer shaft and the other refractive element, 18, is mounted on a longer inner shaft. The two elements are mounted spaced apart from each other with coupling fluid therebetween. One element is held stationary while the other is rotated, or vice versa. Similarly, they are rotated in opposite directions or in the same direction at different speeds. The appropriate drive motor assembly to individually and independently rotate the outer and inner shafts is provided.

Refractive assemblies other than the two wedges are attachable to the two part shaft 13 if desired. A cylindrical plano-convex element and a complementary cylindrical plano-concave element or combinations thereof may be mounted thereon separated from each other by the appropriate distance. One is held stationary while the other is rotated or they are rotated with respect to each other in a particular pattern. This advantageously permits selective deposition of energy over complex contours. Tumors that are treated may be oblong, egg-shaped, football shaped, etc. Two Fresnel lens refractive assemblies separated from each other may be mounted on the two part shaft. Each such assembly may be symmetrical and the two together may also be symmetrical, but moving one with respect to the other or one in an eccentric rotation produces a time averaged energy deposition for tumor treatment. Other combinations of two refractive assemblies using one or more of the refractive assemblies described herein are possible. This feature provides the appropriate deposition of energy to a wide variety of tumors.

Figure 4:
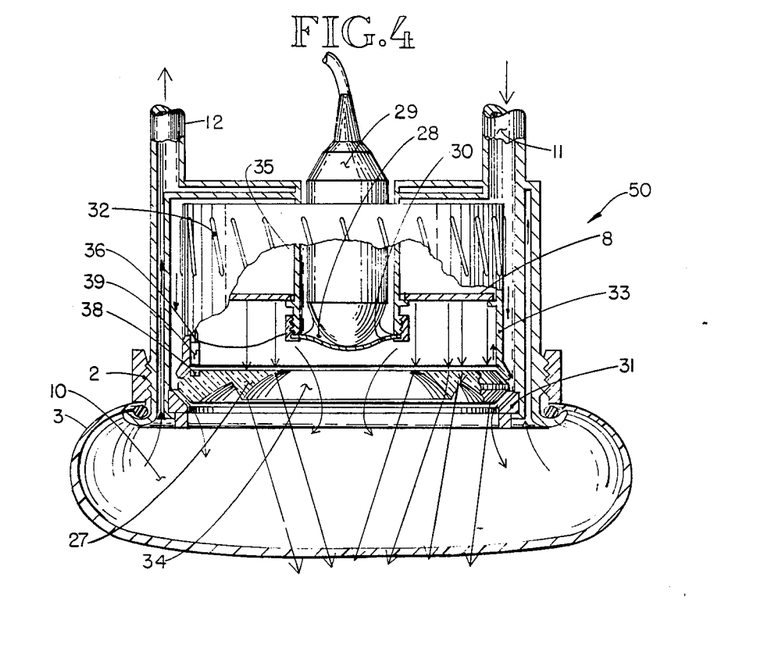
FIG. 4 is a frontal, elevated view of a partial cross section showing an imaging probe and a refractive assembly.

A circulating fluid as the drive mechanism for the hyperthermic ultrasonic assembly 50 is illustrated in FIG. 4. The housing 1 has a transducer 29 for imaging the human body under treatment. The transducer 29 is mounted in the center of the assembly and is rotatable with respect to different axes to provide a three-dimensional view of the tumor under treatment.

A membrane 30 secured in a sealing relationship by threaded ring 36 separates the fluid 10 from the imaging port 35. The imaging transducer 29 may be removed and replaced while maintaining a closed fluid seal in the housing 1. An opening 34 in the refractive assembly 27 allows passage of the acoustic signals from the probe. assembly 27 may provide an imaging lens. Imaging port 35 and transducer 29 are shown centrally disposed but could be placed in a different position if desired.

A transducer assembly 8 providing high energy, hyperthermic ultrasonic waves is provided within the housing 33. The housing 33 has a plurality of vanes 32 arranged along the outer edge of the circular housing assembly 33. Fluid forcibly enters through port 11, and into a concentric passage around housing 33. The fluid is deflected to acquire a tangential velocity component by impinging on vanes 32. In this embodiment a drive motor is not necessary, the circulating fluid causing the motion of the refractive assembly 27 with respect to the stationary transducer. A fluid bearing is created by fluid 10 as it flows through the conical gap between 27 and 33 and 27 and 31. Rotation of the refractive assembly 27 with respect to the transducer 8 alters the ultrasonic energy pattern applied to the body in the manner described herein. The transducer may be a single transducer or an array with each being individually controllable in frequency, amplitude, phase, etc. The refractive assembly 27 may be of a type as described in FIGS. 1, 2b–2f, 3, or other desired element to focus, deflect, or diffuse the ultrasonic energy as needed. An additional vane or horizontal flow of fluid to create lateral movement, regular or non-periodic, of the refractive assembly 27 may be provided near the edge of housing 33.

Figures 5A, 5B, 5C:
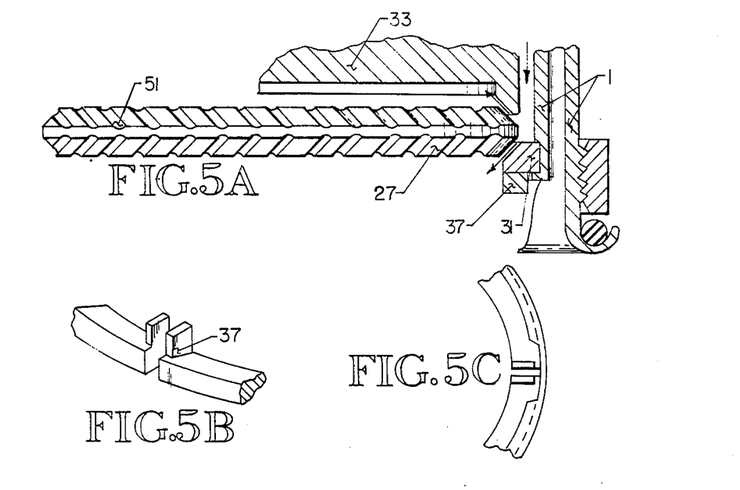
FIGS. 5a–5c are elevated and perspective views illustrating the interchangeability of the refractive assembly.

Alternatively, slots 51, shown in FIG. 5, could be placed on refractive assembly 27 to provide rotation, lateral movement, or combinations thereof. The slots could also be incorporated into the bearing housing 33, the capture ring 31 or other locations as desired to provide the movement of the refractive element 27. A principal advantage of the fluid bearing housing assembly is that no motor shaft or central support structure is required such that the central portion of the transducer is not occluded. Similarly, the central portion of the refractive assembly is not occluded. A centrally located heating transducer could be used in place of, or in cooperation with the imaging transducer. A further advantage is that a separate drive motor to rotate the refractive assembly is not required. An advantage of the fluid bearing assembly of FIG. 4 is the ease of creating and altering the relative movement of the refractive assembly with respect to the transducer.

A motion detector 39 is provided to verify and determine the movement of refractive assembly 27 with respect to the housing 33. The motion detector 39 is a Hall device sensing the presence of one or more ferrous elements 38 embedded in the rim of refractive assembly 27. Alternatively, other sensors to determine the relative movement of the refractive element 27 and transducers could be used.

The refractive element is easily interchangeable. As described herein, specific applications may require different types of ultrasonic patterns for treatment. Different refractive assemblies may be used with the same transducer assembly. A capture ring 31 retains the refractive assembly 27 in place within housing 1. The capture ring 31 includes tabs 37 separated by a small space. Pinching together tabs 37 permits the easy removal of the capture ring 31 and the refractive element 27. A different refractive element may be placed within the transducer assembly housing 1 with the clamp ring, membrane 3 and fluid 10 being replaced for use.

Figure 6:
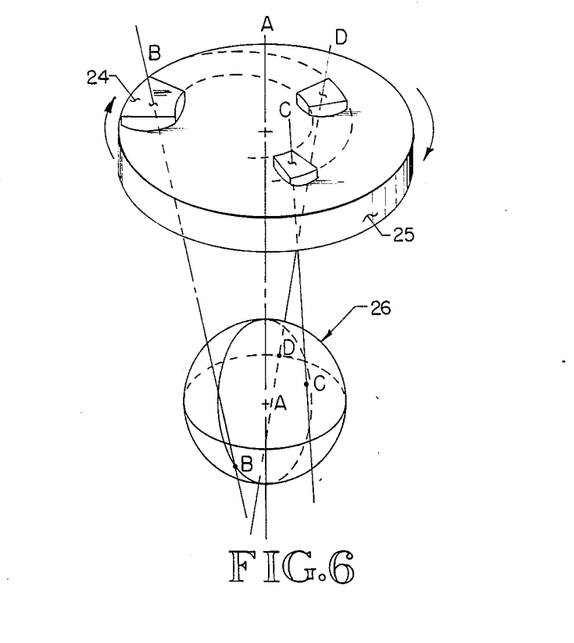
FIG. 6 is an isometric view of a refractive assembly including a large number of lenses which are arranged in a spiral pattern.

FIG. 6 illustrates a spherical refractive assembly 25 similar to the one shown in FIG. 2f. This assembly has various elements or facets 24. A tumor mass 26 to be treated by the ultrasonic energy applied through refractive assembly 25 has surface points D, C, and B, and a central axis portion A. A tumor of this type has rapidly growing cells around the outer portion of the sphere. The rapidly growing cells have a large blood supply which acts to carry off excess heat. The interior portion of the tumor tends to include necrotic tissue. A tumor of this type is best treated by applying controlled amounts of heating along the outer surface of the contour. A high temperature is desired on the surface to effectively treat these cells, while the interior cells are maintained at or below therapeutic levels.

The refractive assembly 25 has numerous lenses or elements, each having a different refractive pattern than the others. The individual refractive elements are distributed over the entire refractive assembly 25 in a spiral pattern about the center of the assembly which is also the axis of rotation, A—A, of the refractive assembly 25. The axis of rotation aligns with a central portion of the tumor, however, the main energy is focused on an area other than the central portion. The tumor may be of arbitrary shape and the refractive assembly, transducer assembly or both moved while energy is applied to the tumor. Movement that is carried out by a mechanical device is preferred to minimize required operator skill.

These refractive elements may be either simple or compound elements. In a preferred embodiment, each of the refractive elements 24 is formed by casting a high sound velocity material, similar to the syntactic foam previously described, and subsequently filling one surface with a low velocity material such as the silicone compound described herein.

The individual elements 24 may have different acoustical refraction characteristics than shown in FIG. 6 if desired. For example, all the elements may be wedge shaped, plano-plano, convex-concave, concave-plano, planoconvex, etc. Alternatively, a combination of different types of elements may be used. Diverging elements may be in the center portion of the assembly. These would direct the energy outward to the outer portions of the tumor. Deflecting, wedge-shaped or plano-plano elements may be in the middle portion of the assembly. These may deflect the energy or average it so it falls on the outer portions of a tumor also. Focusing elements may be at the outer edge of the assembly. These would direct the energy inward to fall on the outer portions of a tumor. Each of the elements cooperate to direct a maximum amount of energy at the surface or other desired location of the tumor with less energy deposited at the other locations. This produces efficient treatment with less overall energy entering the body.

Such a focused device is useful in preferentially heating the surface of near-spherical tumors. By selecting the facets correctly it is possible to uniformly heat a spherical shell of arbitrary depth and diameter. Maximum therapeutic benefit is obtained by heating the tumor surface so that the regions of highest growth are suppressed without unnecessarily taxing the body's ability to clean up necrotic debris within the tumor.

This refractive assembly may be slowly rotated to evenly treat all portions of the tumor. This type of assembly is usable with the apparatus shown in FIGS. 3-5 or fixed to the transducer face as shown in FIGS. 2b-f. The movement coupled with the particular arrangement of refractive elements provides that the near field maxima and minima do not result in hot and cold spots nor deposit excessive energy on healthy tissue or bone.

For focused heating the desired mean value is the same over the periphery of the tumor. Inside and outside the tumor it is generally desired that the tissue receive as little energy as possible. Uniformity in these non-heat regions is not a requirement although hot spots should be avoided. An appropriate selection of refractive elements can approach the desired performance.

We claim:
1. An apparatus for heating a region in a body comprising:
   a housing means for retaining said apparatus;
   a transducer means positioned within said housing for generating an ultrasonic energy pattern that propagates into said region;
   a refractive assembly positioned within said housing and spaced from said transducer means and disposed between said transducer means and said region, through which said ultrasonic energy propagates;
   a coupling medium positioned within said housing and disposed between said transducer means and said refractive assembly and between said refractive assembly and said region; and
   a drive means for moving said refractive assembly relative to said transducer means to alter said ultrasonic energy pattern propagating into said region, said drive means including a circulating fluid contacting said refractive assembly, said drive means also including slots in said refractive assembly in contact with said circulating fluid causing said refractive assembly to move.

2. The apparatus according to claim 1 wherein said drive means rotates the refractive assembly about an axis parallel to the direction of ultrasonic energy propagation from said transducer means through said refractive assembly and into said region.

3. The apparatus according to claim 1 wherein said drive means moves said refractive assembly in a linear movement.

4. The apparatus according to claim 1 wherein said drive means moves said refractive assembly in a combined rotational motion about a first axis, said first axis being in a plane parallel to the direction of ultrasonic energy propagation, linear motion along a second plane, and pivoting motion about a third plane the motion in each of the three planes occurring simultaneously.

5. The apparatus according to claim 1 wherein said transducer means includes a plurality of transducers, each adapted to be driven independently from each other in frequency, phase or amplitude while propagating ultrasonic energy during use.

6. The apparatus according to claim 1 wherein said refractive assembly includes a plurality of refractive elements arranged in a spiral.

7. The apparatus according to claim 1 wherein said refractive assembly includes a plurality of refractive elements each having refraction characteristics that are different than each other.

8. The apparatus according to claim 1 wherein said refractive assembly is coupled to a rotatable shaft.

9. The apparatus according to claim 1 wherein said coupling medium includes said circulating fluid.

10. The apparatus according to claim 1 wherein said drive means further includes fluid jet means for causing forced circulation of said fluid.

11. The apparatus according to claim 1 further including a sensor means for sensing movement of said refractive assembly with respect to said transducer means.

12. The apparatus according to claim 1 further including an imaging probe coupled to said housing and disposed in a position to propagate sound waves through said coupling medium for providing an image of the region being heated.

13. An apparatus for heating a region in a body comprising:
   a housing having a compliant membrane connected in a sealed relationship to said housing with a removable coupling;

a transducer assembly means within said housing for generating an ultrasonic energy pattern that propagates into said region;

a refractive assembly within said housing spaced from said transducer assembly means and disposed between said transducer assembly means and said region through which said ultrasonic energy propagates;

a fluid within said housing in contact with said refractive assembly, said fluid being disposed between said transducer assembly means and said refractive assembly and between said refractive assembly and said membrane; and drive means for forcibly circulating said fluid causing said refractive assembly to move relative to said transducer assembly means to alter said ultrasonic energy pattern propagating into said region.

14. An apparatus according to claim 13 further including vanes on said transducer assembly means to alter the circulation movement pattern of said circulating fluid.

15. An apparatus according to claim 13 further including slots on said refractive assembly to cause movement of said refractive assembly by said circulating fluid.

16. An apparatus comprising:
an integral refractive assembly having a plurality of individual refractive elements;
a plurality of said refractive elements providing a refractive pattern of ultrasonic energy different from each other when placed in the path of a propagating ultrasonic energy pattern; and
said integral refractive assembly being nonsymmetrical in all planes.

17. The refractive assembly of claim 16 wherein said elements are arranged in a spiral pattern.

18. The refractive assembly of claim 16 further including a transducer for generating said propagating ultrasonic energy pattern into a region of a body, said refractive assembly being located external to said body and disposed in the path of propagating ultrasonic energy between said transducer and said region.

19. The apparatus according to claim 18 wherein said refractive assembly is directly attached to said transducer.

20. The apparatus according to claim 18 wherein said refractive assembly is spaced from said transducer and a fluid is disposed therebetween, said fluid being enclosed in a housing.

21. The method of heating a region in a body, comprising:
transmitting an ultrasonic energy pattern from a transducer into said region, said ultrasonic energy pattern having a plurality of different energy intensities propagating into said region;
positioning a refractive assembly between said transducer and said region, said refractive assembly having slots on an outer surface thereof; and
forcibly circulating a fluid in contact with said refractive assembly causing said refractive assembly to move under the force imparted by said circulating fluid.

22. The method according to claim 21 wherein said movement is rotational movement about an axis of rotation.

23. The method according to claim 22 further including the steps of:
pivoting said refractive assembly about an axis orthogonal to the axis of rotation.

24. The method according to claim 21 wherein said movement is a combination of rotational and linear movement.

25. The method according to claim 21 wherein said acoustic pattern includes maxima and minima, said pattern being moved to more uniformly apply acoustic energy into said region.

26. A refractive assembly comprising:
a unitary integral member having a plurality of individual refractive elements that refract ultrasonic energy passing therethrough at an angle with respect to a central axis of said refractive assembly, each of said refractive elements bending the ultrasonic energy at a different angle than each of the other refractive elements of said refractive assembly, said refractive elements being arranged in the form of a spiral, extending from a central axis, outward.

* * * * *